(12) United States Patent
Oh et al.

(10) Patent No.: US 8,956,629 B2
(45) Date of Patent: Feb. 17, 2015

(54) DENTAL COMPOSITION CONTAINING ORGANIC NANOTUBE

(75) Inventors: Myung-Hwan Oh, Seoul (KR); Won-Ho Kim, Incheon (KR); Mi Hyoun Ham, Incheon (KR); Jong-Hwi Lee, Seoul (KR); Yun-Ki Kim, Anyang-si (KR)

(73) Assignee: Vericom Co. Ltd, Gyeonggi-Do (KR)

( * ) Notice: Subject to any disclaimer, the term of this patent is extended or adjusted under 35 U.S.C. 154(b) by 435 days.

(21) Appl. No.: 12/993,090

(22) PCT Filed: May 19, 2008

(86) PCT No.: PCT/KR2008/002788
§ 371 (c)(1),
(2), (4) Date: Nov. 22, 2010

(87) PCT Pub. No.: WO2009/142340
PCT Pub. Date: Nov. 26, 2009

(65) Prior Publication Data
US 2011/0064776 A1    Mar. 17, 2011

(51) Int. Cl.
| | |
|---|---|
| *A61K 33/16* | (2006.01) |
| *A61K 9/00* | (2006.01) |
| *A61K 31/155* | (2006.01) |
| *A61P 1/02* | (2006.01) |
| *A61P 31/04* | (2006.01) |
| *B82Y 5/00* | (2011.01) |
| *A61K 6/083* | (2006.01) |
| *A61K 6/00* | (2006.01) |
| *A61K 6/09* | (2006.01) |

(52) U.S. Cl.
CPC .............. *A61K 6/083* (2013.01); *A61K 6/0067* (2013.01); *A61K 6/09* (2013.01); *Y10S 977/919* (2013.01)
USPC ........... 424/400; 424/673; 523/115; 523/116; 514/635; 514/643; 977/919

(58) Field of Classification Search
None
See application file for complete search history.

(56) References Cited

U.S. PATENT DOCUMENTS

| | | | | |
|---|---|---|---|---|
| 5,718,924 | A | * | 2/1998 | Braden et al. .................. 424/673 |
| 6,326,417 | B1 | | 12/2001 | Jia |
| 6,599,961 | B1 | * | 7/2003 | Pienkowski et al. .......... 523/120 |
| 6,703,518 | B1 | | 3/2004 | Xu |
| 6,872,403 | B2 | | 3/2005 | Pienkowski |
| 2003/0153965 | A1 | | 8/2003 | Supronowicz |
| 2004/0076681 | A1 | * | 4/2004 | Dennis et al. .................. 424/489 |
| 2007/0043142 | A1 | | 2/2007 | Dodiuk-Kenig |

FOREIGN PATENT DOCUMENTS

| | | |
|---|---|---|
| JP | 10-1998-025218 | 1/1998 |
| JP | 10-2008-025218 | 1/1998 |
| KR | 10-2007-0121894 | * 10/2007 |
| KR | 10-2007-0121894 | 12/2007 |
| KR | 20060056699 | * 12/2007 |

OTHER PUBLICATIONS

Andreas Greiner and Joachim H. Wendorff. Electrospinning: A Fascinating Method for the Preparation of Ultrathin Fibers, Angew. Chem. Int. Ed. 2007, 46, 5670-5703.*
K.J. Anusavice, N.-Z. Zhang and C. Shen. Effect of CaF2 Content on Rate of Fluoride Release from Filled Resins, J Dent Res 2005 84: 440-445.*
English machine translation of KR102007-0121894; translation supplied by Korean Patent Office.*
S.K. Smart, A.I. Cassady, G.Q. Lu, D.J. Martin. The biocompatibility of carbon nanotubes. Carbon 44 (2006) 1034-1047.*
Andreas Greiner and Joachim H. Wendorff. Electrospinning: A Fascinating Method for the Preparation of Ultrathin Fibers. Angew. Chem. Int. Ed. 2007, 46, 5670-5703.*
Definition of "porous"; by Merriam-Webster online: "having small holes that allow air or liquid to pass through; easy to pass or get through" (downloaded Apr. 20, 2014, from the internet site: http://www.merriam-webster.com/dictionary/porous).*
"Susceptibility of Oral Bacteria to Various Fluoride Salts" by M. Maltz and C.G. Emilson (J Dent Res 61: 786-791), and published Jun. 1982.
Cao (J Dent Res 73.Abstr. 675), published 1994.
"Disposition of fluoride on enamel surfaces released from varnishes is limited to vicinity of fluoridation site" by T. Attin, et. al. (Clin Oral Invest 11: 83-88), and published on Oct. 17, 2006.
"Augmentation of acrylic bone cement with multiwall carbon nanotubes" by Brock Mans, et. al., published online Jan. 3, 2006.
Brock Marrs, et al. "Augmentation of Acrylic Bone Cement with Multiwall Carbon Nanotubes", Journal of biomedical materials research. Part A, 2006, v.77A. No. 2, pp. 269-276. ( To Follow Later).
PCT Search Report from PCT/KR2008/002788 dated Jan. 9, 2009.
PCT International Preliminary Report on Patentability Chapter I (with Written Opinion) from PCT/KR2008/002788 dated Nov. 23, 2010.

* cited by examiner

Primary Examiner — Frederick Krass
Assistant Examiner — Michael P Cohen
(74) Attorney, Agent, or Firm — Ladas & Parry, LLP

(57) ABSTRACT

Disclosed is a dental composition, comprising unsaturated double bond-containing monomers and/or oligomers, a catalytic amount of polymerization initiator to initiate polymerization, and a filler, wherein the dental composition comprises an organic nanotube containing an antibacterial or anticariogenic material to inhibit or prevent tooth decay.

The dental composition comprises an organic nanotube containing an antibacterial or anticariogenic material, thus uniformly and continuously exhibiting anticariogenic and antibacterial activities, while avoiding deterioration in physical properties required for the dental material.

9 Claims, 2 Drawing Sheets

DENTAL COMPOSITION CONTAINING ORGANIC NANOTUBE

FIELD OF THE INVENTION

The present invention relates to a dental composition containing an organic nanotube. More specifically, the present invention relates to a dental composition comprising: unsaturated double bond-containing monomers and/or oligomers; a catalytic amount of polymerization initiator to initiate polymerization; and a filler, wherein the composition comprises an organic nanotube containing an antibacterial or anticariogenic material to inhibit or prevent tooth decay.

BACKGROUND OF THE INVENTION

Dental compositions such as dental restorative materials, dental adhesives and dental cosmetic compositions are used for restoring dental cavities caused by factors such as tooth decay and caries.

In particular, dental restorative materials are essential dental materials widely utilized in a variety of applications including general dental treatments to restore sites broken by dental caries or trauma or the overall crown or to fix mobile teeth, and orthodontic or cosmetic dental treatments.

Amalgam composed of alloys and mercury has been conventionally used as dental restorative materials, but polymeric dental restorative materials (PDRMs) substitute for amalgams due to problems such as toxicity to humans and environmental pollution, and a great deal of research associated therewith has been conducted.

Since the late 1940s, a method for directly filling dental cavities with a mixture of tertiary amine-containing methacrylate monomers and benzoyl peroxide-containing polymeric powders, based on the fact that the mixture hardens at ambient temperature has been suggested. This method has been commercially available and clinically used in the U.S. since the 1950s, but was not used over a long time due to disadvantages such as transparency, high polymerization shrinkage, low color stability and hardness and lack of adhesion to teeth.

In 1951, Knock and Glenn introduced a novel restorative material and suggested a solution to the polymerization shrinkage by introducing inorganic fillers into resins. In the early 1950s, Bjorksten and Yeager introduced silane coupling agents into the surface of inorganic fillers and this method was embodied by Bowen in American National Standards Institute.

Bowen developed Bis-GMA (bisphenol A diglycidylether methacrylate) wherein methylmethacrylate is introduced into epoxy monomers in 1956 and Bis-GMA-introduced resins in 1962. In 1965, Bowen was issued a patent for a resin containing a blend of Bis-GMA with silanized quartz particles and this resin is now the most widely used dental composite.

Since the 1970s, polymeric dental restorative materials have been practically applied to dental treatments. For the early 10 years, PDRMs were used as alternatives or substitutes for silicate cement for class 3, 4 and 5 cavities. Only in the 1990s were PDRMs applied in earnest to stress-bearing molar areas, Class 1 and 2 cavities.

Such recent application is closely related to fears of patients undergoing dental treatment concerning mercury contained in dental amalgams and increased demand for aesthetic operations. Furthermore, this is due to improvement in functions of dental materials associated with these phenomena.

Unlike general materials, these dental compositions require a variety of properties due to the unique environment of the oral cavity. Specifically, dental compositions must be prepared taking into consideration various factors such as humid environments in which relative humidity is about 100%, occlusal force upon chewing, rapid temperature variation, close contact with oral soft tissues, frequent side effects such as hypersensitivity and various bacteria species present in oral cavities. Other requirements are aesthetic desires of individuals in accordance with recent development of mass media and color harmony with teeth.

In particular, anticariogenic activity to other hard tissues of teeth such as various dentins, cementum and/or enamels is considerably essential and important for dental compositions.

Accordingly, a great deal of research has been conducted to improve anticariogenic activity. For example, U.S. Pat. No. 6,326,417 discloses dental composites into which organic antibacterial materials are introduced. In addition, Japanese Patent Application Publication No. 1998-025218 discloses antibacterial fillers wherein the surface of inorganic fillers is coated with polymeric monomers including at least one antibacterial monomer. However, such an organic antibacterial agent or antibacterial filler has disadvantages of pigmentations and deteriorated physical properties.

In particular, a great deal of research associated with antibacterial and anticariogenic effects of fluorine has been conducted, and fluorine, which has been known since the early 1940s, exhibits anticariogenic activity to hard tissues of teeth and thus possesses high biological significance.

Maltz and Emilson (*J Dent Res* 61: 786-791) reported that fluorine at a concentration of 0.019 to 0.14 ppm exhibits inhibitory effects upon bacterial growth, and Cao et al., (*J Dent Res* 73. Abstr. 675) announced that when fluorine is continuously present at a concentration as low as 0.01 ppm, it is effective for recalcification of various lesions and inhibition of caries. In addition, Attin et al., (*Clin Oral Invest* 11: 83-88) reported that fluorine at a concentration of 0.04 ppm inhibits various growth.

In vitro research has demonstrated that, as depicted in the following reaction scheme, fluorine is chemically bonded to hydroxyapatite of tooth substrates to form antiacidic fluoroapatite, reinforcing teeth. In addition, fluorine inhibits formation of glucane by glucose transferase in the process of bacterial metabolism in oral cavities.

$$Ca_{10}(PO_4)_6(OH)_2 + 2F^- \rightarrow Ca_{10}(PO_4)_6F_2 + 2OH^- \quad (1)$$

Accordingly, introduction of fluorine into dental materials inhibits decalcification of teeth and improves recalcification thereof, thereby advantageously inhibiting production of carbohydrates and formation of tartar by bacteria fermentation. That is, fluorine also reinforces teeth, thus performing an important major function for designing materials imparting permanence to adhesion to dentine.

Meanwhile, of dental composition ingredients, polymeric resins disadvantageously shrink upon polymerization, thus providing a space between teeth and restorative materials and leading to a micro-leakage. In this case, bacteria may permeate the space provided between teeth and restorative materials, inducing secondary caries. Accordingly, whether or not anticariogenic activity is exerted is a considerably important issue.

Accordingly, in an attempt to prevent secondary caries caused by polymeric resins, research associated with fluoride-containing dental restorative materials wherein a tooth substrate constituting cavity walls is fluoridized with fluoride ions released from fluoride in order to reinforce the tooth substrate has been conducted.

For example, U.S. Pat. No. 6,703,518 discloses research associated with fluorine-releasing compositions. This patent also discloses research associated with fluorine-releasing materials such as fluorine-releasing copolymers, fluoroaluminosilicate glasses, metal fluorides and ammonium fluorides.

Application of these technologies is limited due to problems such as considerably low fluoride ion release level, deterioration in mechanical properties upon fluorine release and undesired release behaviors of fluoride ions wherein the fluoride ions are rapidly released only in an initial stage, but release thereof gradually decreases.

Accordingly, there is an urgently increasing need for technology development associated with dental compositions, i.e., dental restorative materials that exhibit superior mechanical properties and aesthetic effects and continuously exert uniform anticariogenic activity so as to inhibit or prevent decay of hard tissues of teeth.

SUMMARY OF THE INVENTION

Therefore, the present invention has been made in view of the above problems of the prior arts.

As a result of a variety of extensive and intensive studies and experiments, the inventors of the present invention have discovered that addition of an organic nanotube containing an antibacterial or anticariogenic material, to inhibit or prevent tooth decay, to a dental composition comprising unsaturated double bond-containing monomers and/or oligomers as a base material enables maintenance of physical properties required for dental materials, such as mechanical strength and aesthetic effects, and uniform and continuous anticariogenic and antibacterial activities to hard tissues of teeth. Accordingly, the present invention is finally completed, based on the afore-mentioned discovery.

In accordance with an aspect of the present invention, the above and other objects can be accomplished by the provision of a dental composition comprising: unsaturated double bond-containing monomers and/or oligomers; a catalytic amount of polymerization initiator to initiate polymerization; and a filler, wherein the composition comprises an organic nanotube containing an antibacterial or anticariogenic material (antibacterial/anticariogenic material) to inhibit or prevent tooth decay.

DETAILED DESCRIPTION OF PREFERRED EMBODIMENTS

Hereinafter, the present invention will be described in detail.

The term "nanotube" as used herein refers to a nano-scale tubular material and may include nanofibers. The nano-scale is defined as the range of 1 nm to 3,000 nm. In addition, the term "antibacterial/anticariogenic material-containing nanotube" as used herein refers to an organic nanotube which contains an antibacterial or anticariogenic material.

There are two mechanisms whereby the antibacterial/anticariogenic material is released from the dental composition. One is that the antibacterial/anticariogenic material diffuses from the composition to the inside of the oral cavity. This mechanism is affected by a diffusion coefficient of the antibacterial/anticariogenic material. The other is that the dental material is dissolved, thus releasing the antibacterial/anticariogenic material. This mechanism is affected by degradation of the material surface.

In accordance with the dental composition of the present invention, the antibacterial/anticariogenic material-containing nanotube is homogeneously distributed in the dental composition and the antibacterial/anticariogenic material is released from the nanotube. For this reason, the dental composition releases according to the first mechanism. Alternatively, the dental composition may show release behaviors according to the second mechanism due to abrasion of the dental composition by chewing or brushing.

Accordingly, the dental composition can both initially and continuously exhibit release effects of the antibacterial/anticariogenic material.

Specifically, both terminals of the nanotube are open providing pathways allowing the antibacterial/anticariogenic material to be released from the antibacterial/anticariogenic material-containing nanotube, thus preventing release of a great amount of antibacterial/anticariogenic material within a short time. Accordingly, anticariogenic activity to hard tissues of teeth can be continuously maintained around the teeth to which the dental composition is applied.

Furthermore, despite the antibacterial/anticariogenic material being released, the antibacterial/anticariogenic material containing nanotube can maintain the shape and volume of the organic nanotube and exert filling effects, thus advantageously avoiding deterioration in strength of the dental composition by release of antibacterial/anticariogenic material.

The organic nanotube is made of an organic material and thus has affinity with an organic matrix constituting a base material prepared through polymerization of unsaturated group-containing monomers and/or oligomers. Accordingly, the organic nanotube can be readily mixed with the organic matrix and dispersed therein. Preferably, the organic nanotube may be a material which has high affinity with the organic matrix. The term "high affinity" as used herein means a property of a material wherein the material has physical and chemical properties similar to an organic matrix and is thus mixed with the organic matrix, causing no phase-separation. For example, the high-affinity material is selected from the group consisting of methacryl, acryl, epoxy, styrene and urethane polymers, and combinations and copolymers thereof.

The organic nanotube may have a hollow in which the antibacterial/anticariogenic material is contained. Alternatively, the organic nanotube may have a porous external surface, taking into consideration a release amount of the desired antibacterial/anticariogenic material.

The size of the organic nanotube may be suitably controlled, taking into consideration factors such as dispersion in the organic matrix, aesthetic effects, and the size or content of antibacterial/anticariogenic material, and is preferably 10 to 3,000 nm in diameter, more preferably 50 to 1,000 nm. In addition, the organic nanotube may be obtained by suitably cutting continuous lengths of organic nanotubes in a desired size, taking into consideration the size of the filler and is preferably 0.1 to 100 μm in length, more preferably, 0.5 to 10 μm.

Herein, when considering easy release of the antibacterial/anticariogenic material, it is preferable that the antibacterial/anticariogenic material simply contain the organic nanotube without additional bonding to the organic nanotube. However, the case wherein the antibacterial/anticariogenic material is physically or chemically bonded to an organic nanotube is not excluded from the scope of the present invention.

The antibacterial/anticariogenic material is non-toxic for teeth and the human body and exhibits anticariogenic activity on hard tissues of teeth Examples of antibacterial/anticariogenic materials include organic, inorganic and natural antibacterial/anticariogenic materials. Examples of organic antibacterial/anticariogenic materials include chlorhexidine and/ or benzalkonium chlorides, etc. Examples of inorganic antibacterial/anticariogenic materials include zirconiums, zeolites and calcium phosphates. Examples of natural antibacterial/anticariogenic materials include chitosans.

In an exemplary embodiment, the antibacterial/anticariogenic material may be a fluorine compound. As mentioned above, fluorine is an anticariogenic material for hard tissues of teeth, which prevents decalcification of a tooth substrate and improves recalcification, thereby advantageously inhibiting production of carbohydrates and formation of tartar by bacteria fermentation and reinforcing the tooth substrate.

In order to continuously exhibit antibacterial or anticariogenic activities, fluorine may be preferably in the form of sustained-release preparations and, for this purpose, the fluorine compound serving as a fluorine source may be metal fluoride, ammonium fluoride and a mixture thereof. More specifically, the fluorine compound is selected from the group consisting of aluminum fluoride, sodium fluoride, calcium fluoride, magnesium fluoride, potassium fluoride and combinations thereof, and is not limited thereto.

When the antibacterial/anticariogenic material containing nanotube is added in an excessively great amount, a surface area increases and a viscosity thus increases. As a result, problems such as significantly deteriorated dispersability, difficulty of securing transparency due to coagulation and poor workability upon operation occur. On the other hand, when the antibacterial/anticariogenic material containing nanotube is used in an excessively small amount, it is quite difficult for the antibacterial/anticariogenic material to be released in a desired content. In view of these concerns, the organic nanotube is preferably present in an amount of preferably 0.05 to 7% by weight, more preferably 0.1 to 5% by weight, based on the total weight of the composition.

The present invention is not particularly limited as to a method for preparing the antibacterial/anticariogenic material containing nanotube. For example, a porous and/or hollow organic nanotube in which the antibacterial/anticariogenic material is contained is prepared and an antibacterial/anticariogenic material is then introduced into the organic nanotube. Alternatively, the organic nanotube is prepared, while containing the antibacterial/anticariogenic material. At this time, methods such as template, phase-separation, self-assembly, melt-blowing, co-axial spinning, electrospinning and co-axial electrospinning may be used. Of these, co-axial electrospinning is preferred, in that the nanotube can be easily and rapidly prepared in a simple manner and may be have various shapes of single, double and hollow fibers depending on preparation conditions.

A method for preparing the antibacterial/anticariogenic material containing nanotube by co-axial electrospinning is schematically shown in FIG. 1. Referring to FIG. 1, an inner solution containing an antibacterial/anticariogenic material as a core material is injected into an inner nozzle, a sheath solution containing an organic material (e.g., molten polymer) constituting the external surface of a nanotube is injected into an external nozzle, and spinning is performed at a high voltage, thereby integrally preparing an antibacterial/anticariogenic material containing nanotube. At this time, a porous structure may be formed by controlling the type or evaporation rate of solvents used for the solution. Specific process conditions and methods of the co-axial electrospinning are well-known in the art and a detailed explanation thereof is omitted.

In the present invention, any unsaturated double bond-containing monomers and/or oligomers may be used without particular limitation so long as they are dental materials with high mechanical strength and are polymerizable. Preferred is the use of methyl methacrylate (MMA).

Examples of methyl methacrylate (MMA) include, but are not limited to, 2,2-bis-(4-(2-hydroxy-3-methacryloyloxypropoxy)phenyl)propane (Bis-GMA), ethylene glycol dimethacrylate (EGDMA), triethylene glycol dimethacrylate (TEGDMA), ethoxylate bisphenol A dimethacrylate (Bis-EMA) and urethane dimethacrylate (UDMA). The MMA may be used singly or in combination thereof.

The unsaturated double bond-containing monomers and/or oligomers may be varied according to applications and desired use thereof and is not particularly limited. When the content of the monomers and/or oligomers is excessively low, it is difficult to form desired polymers and to mix with an inorganic filler. On the other hand, when the content is excessively high, workability is disadvantageously deteriorated due to increased flowability. When taking into consideration these issues, the monomers and/or oligomers are preferably in an amount of 10 to 99% by weight, more preferably 10 to 90% by weight, based on the total weight of the composition.

The composition and content of the unsaturated double bond-containing monomers and/or oligomers have a great influence on factors such as dispersability of the dental composition upon polymerization and are important for determining polymerization shrinkage and workability.

In an exemplary embodiment, MMA used for the dental composition may be present in a ratio of Bis-GMA:UDMA:TEGDMA=1 to 3:0.2 to 2:0.2 to 2, taking into consideration factors such as desired mechanical properties and low polymerization shrinkage and superior workability. Based on the total weight of the composition, Bis-GMA may be preferably present in an amount of 10 to 20% by weight, and TEGDMA and UDMA are preferably present in an amount of 1 to 10% by weight.

The polymerization initiator may be a photoinitiator. If necessary, the polymerization initiator may further comprise a photo-accelerator. Examples of photoinitiators include: tertiary amine initiators; mixtures (25:75) of diphenyliodonium chloride, diphenyliodonium hexafluorophosphate, diphenyliodonium tetrafluoroborate and tolylcumyliodoniumtetrakis (pentafluorophenyl)borate, acyl and bisacyl phosphine oxides, bis(2,4,6-trimethylbenzoyl)phenylphosphine oxide, bis(2,6-dimethoxybenzoyl)-(2,4,4-trimethylpentyl)phosphine oxide or bis(2,6-dimethoxybenzoyl)-2,4,4-trimethylpentylphosphine oxide, and 2-hydroxy-2-methyl-1-phenyl-propan-1-one; mixtures (1:1) of bis(2,4,6-trimethylbenzoyl) phenyl phosphine oxide and 2-hydroxy-2-methyl-1-phenylpropan-1-one; and ethyl 2,4,6-trimethylbenzylphenyl phosphinate, and the like. In addition, examples of useful photo-accelerators include benzyl, puryl, 3,3,6,6-tetramethylcyclohexanedione, phenanthraquinone, 1-phenyl-1,2-propanedione, 1-aryl-2-alkyl-1,2-ethanedione, cyclic α-diketone and the like. Preferably, camphorquinone (CQ) may be used.

The photopolymerization initiator and photo-accelerator may be contained in the composition, within the range, i.e., in a catalytic amount that they do not injure physical properties of final products. Preferably, based on the total weight of the composition, the photopolymerization initiator and the photo-accelerator are present in an amount of 0.1 to 3% by weight or less, more preferably 1% by weight or less, respectively.

Examples of useful fillers for the present invention include inorganic fillers, organic fillers and fluorine releasing agents.

More specifically, examples of inorganic fillers include, but are not limited to: radiopaque glass powders such as amorphous synthetic silica, crystalline natural silica, barium aluminum silicate, caoline, talc and strontium aluminum silicate; acid-reactive fillers, and nano zirconia fillers. The inorganic filler may be used singly or in combination thereof.

Generally, the inorganic filler is hydrophilic and is thus immiscible with hydrophobic organic monomers and/or oligomers. Accordingly, the inorganic filler may comprise a binder and be surface-treated with a silane coupling agent in order to improve affinity with monomers. Examples of specific hydrophobic surface-treating agents of the inorganic filler are well-known in the art and a detailed explanation thereof is omitted.

The organic filler may be pelletized to an average diameter of 0.005 to 100 μm by synthesizing monomers, which are polymerized from a dental restorative composition to constitute a matrix, or are compatible therewith, by bulk polymerization, emulsion polymerization or suspension polymerization and preparing in the form of a powder. If necessary, mechanical strength can be improved by increasing the cured molecular weight of the monomers, instead of adding an inorganic or organic filler.

The inorganic filler and/or organic filler may be present in an amount of 1 to 90% by weight, based on the total weight of the composition, when taking into consideration a content ratio between the unsaturated double bond-containing monomers and/or oligomers, and the organic nanotube.

The inorganic filler and/or organic filler may have an average diameter of 0.005 to 100 μm. When the average diameter is less than 0.005 μm, the filler may not be uniformly dispersed in the composition due to cohesion between particles. On the other hand, an average diameter higher than 100 μm disadvantageously causes deteriorated texture and decreased workability, making it difficult for operators to apply the composition to teeth, and furthermore results in deteriorated gloss, when large particles are lost by abrasion after curing.

The dental composition of the present invention may be variably used as a dental material. Examples of suitable dental materials include restorative materials, adhesives, implant materials, artificial crowns, fillers for premolars, dental investments, cavity liners, cements, coatings, orthodontic devices, prosthetic materials, sealants and temporary fillers.

Dental restorative materials are major dental materials which are widely utilized in a variety of applications including restoration of damaged sites, orthodontics and cosmetic dental treatments. Accordingly, continuous anticariogenic action to hard tissues of teeth is significantly required. As a result, a dental restorative composition with superior physical properties and continuous anticariogenic activity can be prepared from the organic nanotube-containing dental composition of the present invention used as a dental restorative material.

The dental adhesive may be used to reinforce adhesion of dental restorative materials or to bond restorative materials such as implants or gold crowns applied to gums.

BRIEF DESCRIPTION OF THE DRAWINGS

The above and other aspects, features and other advantages of the present invention will be more clearly understood from the following detailed description taken in conjunction with the accompanying drawings, in which.

EXAMPLES

Now, the present invention will be described in more detail with reference to the following Examples. These examples are provided only for illustrating the present invention and should not be construed as limiting the scope and spirit of the present invention.

Preparation Example 1

Figure 1:
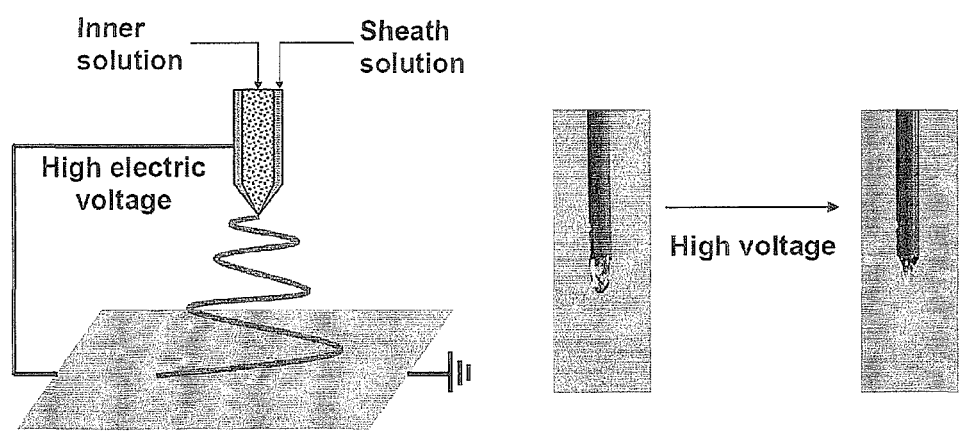
FIG. 1 is a schematic diagram illustrating a process for preparing an antibacterial material-containing nanotube according to one embodiment of the present invention.
Figure 2:
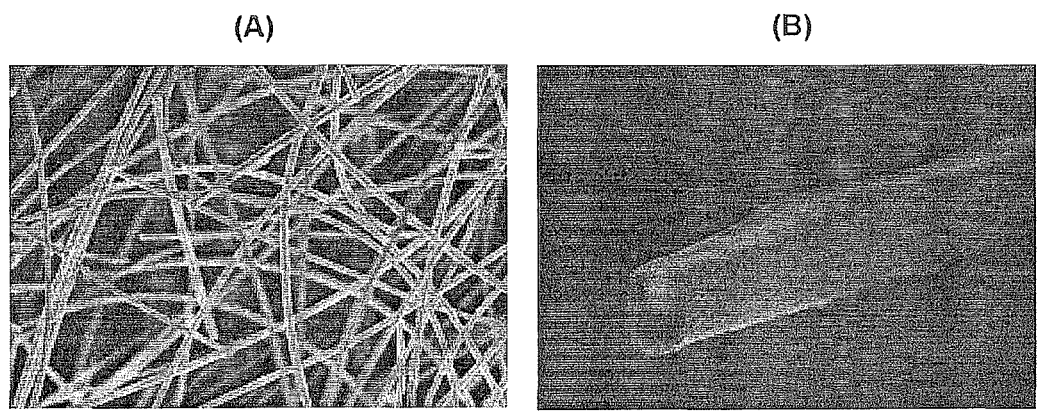
FIG. 2 is an SEM image of the organic nanotube prepared in FIG. 1 (A: 1,000× magnification, B: 11,000× magnification)

An inner nozzle was filled with a solution of sodium fluoride as an antibacterial/anticariogenic material in dimethyl formamide (DMF), an outer nozzle was filled with a solution of polymethyl methacrylate (PMMA) in DMF, electrospinning was performed at a voltage of 16 V and the nozzles were then dried at ambient temperature to prepare a sodium fluoride-containing PMMA nanotube (hereinafter, simply referred to "fluorine-release organic nanotube"). The sodium fluoride contained in the nanotube thus prepared was present in an amount of 10 wt %, with respect to the total weight of the fluorine-release organic nanotube. A scanning electron microscope image of the fluorine-release organic nanotube is shown in FIG. 2.

Example 1

1. Preparation of Photopolymerized Dental Restorative Composition

In accordance with the composition shown in Table 1 below, a photopolymerized dental restorative composition was prepared from the fluorine-release organic nanotube prepared in Example 1.

TABLE 1

| Ingredients | Content (% by weight) |
|---|---|
| 2,2-bis-(4-(2-hydroxy-3-methacryloylpropoxy)phenyl) propane (Bis-GMA) | 15 |
| Triethylene glycol dimethacrylate (TEGDMA) | 5 |
| Urethanedimethacrylate (UDMA) | 5 |
| Barium aluminosilicate | 65.8 |
| Amorphous synthetic silica | 7 |
| Fluorine-release organic nanotube | 0.5 |
| Mix stabilizer of phenol and phosphite | 0.1 |
| Polymerization inhibitor (butyl hydroxy toluene) | 0.1 |
| Camphorquinone | 0.5 |
| Ethyl 4-(N,N-dimethylamino)benzoate | 1.0 |

Example 2

A photopolymerized dental restorative composition was prepared in the same manner as in Example 1 except that the fluorine-release organic nanotube was added in an amount of 1% by weight and barium aluminosilicate was added in an amount of 65.3% by weight.

Example 3

A photopolymerized dental restorative composition was prepared in the same manner as in Example 1 except that the fluorine-release organic nanotube was added in an amount of 3% by weight and barium aluminosilicate was added in an amount of 63.3% by weight.

Example 4

A photopolymerized dental restorative composition was prepared in the same manner as in Example 1 except that the fluorine-release organic nanotube was added in an amount of 5% by weight and barium aluminosilicate was added in an amount of 61.3% by weight.

Comparative Example 1

A photopolymerized dental restorative composition was prepared in the same manner as in Example 1 except that the fluorine-release organic nanotube was not added and barium aluminosilicate was added in an amount of 66.3% by weight.

Comparative Example 2

A photopolymerized dental restorative composition was prepared in the same manner as in Example 1 except that sodium fluoride was added in an amount of 0.5% by weight, instead of a fluorine-release organic nanotube.

Comparative Example 3

A photopolymerized dental restorative composition was prepared in the same manner as in Example 1 except that a fluoroaluminosilicate glass was used instead of barium aluminosilicate, and pyromellitic glycerol dimethacrylate and Bis-GMA required for activating the fluoroaluminosilicate glass fluorine were added in an amount of 5% by weight and 10% by weight, respectively.

Experimental Example 1

The fluorine-release behaviors of the 6 dental restorative compositions prepared in Examples 1 to 4 and Comparative Examples 2 to 3 were evaluated. The fluorine-release behaviors were evaluated using cylindrical specimens. The specifications of the specimens used for the fluorine-release behavior evaluation were 7 mm in diameter and 4 mm in height. The specimens thus manufactured were stored under humid conditions similar to those of the oral cavity for one hour and were then immersed in deionized water over periods of time from one hour to 60 days. An ion-specific electrode calibrated with a standard solution was used to measure the concentration of fluorine ions. The results thus obtained are shown in a graph of FIG. 3.

Figure 3:
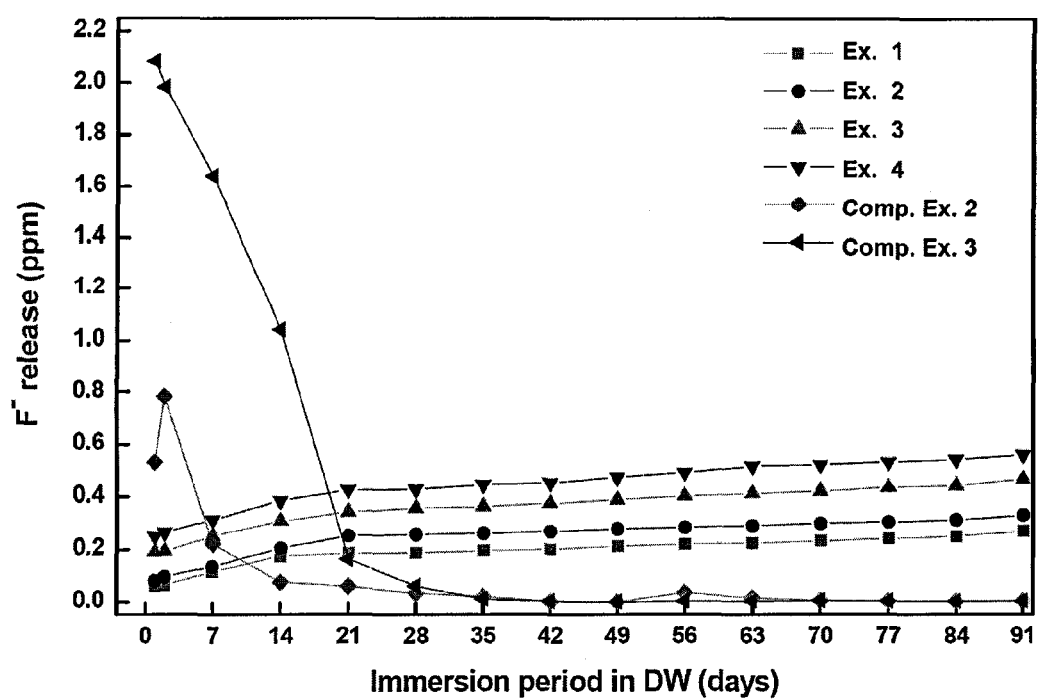
FIG. 3 is a graph showing a fluorine-release behavior of the dental compositions prepared in Examples 1 to 4 and Comparative Examples 2 to 3.

Referring to FIG. 3, in Comparative Example 2 wherein sodium fluoride is directly added, a cured resin has a decreased diffusion coefficient, thus making release of fluorine distributed therein difficult and inducing release of only fluorine present around the surface. Within 14 days, the fluorine present around the surface was mostly exhausted and thereafter no substantial fluorine-release was shown.

Meanwhile, in Comparative Example 3 wherein fluoroaluminosilicate was used, in an initial stage, overall fluorine present on the surface and the inside was released, allowing an excessive amount of fluorine to be released. That is, two Comparative Examples showed no sustained-release due to the absence of a device for controlling fluorine release.

On the other hand, for the dental compositions prepared in Examples 1 to 4 according to the present invention, fluorine was released in a constant amount of 0.1 to 0.6 ppm and was released continuously over 90 days or longer, which indicates sustained-release of fluorine. The reason for these results was that fluoride is contained in the nanotube and release pathways of the fluorine are limited to only both ends. In addition, the amount of fluorine released increases, as the content of nanotube increases. This behavior is due to the fact that, as the content of organic nanotube increases, the content of fluorine increases.

Experimental Example 2

Flexural strength, water absorbance and solubility of a total of five specimens prepared in Examples 1 to 4 and Comparative Examples 1 to 3 were measured. Flexural strength, water absorbance and solubility were measured in accordance with the ISO 4049:2000 standard, under the conditions that flexural strength was measured on the $1^{st}$ and $60^{th}$ days, while storing the compositions at 37° C. over a period of 60 days. Then, the effect of flexural strength on physical properties of the composition after fluorine-release was evaluated. The water absorbance and solubility were measured in accordance with the standard. The results thus obtained are shown in Table 2 below.

TABLE 2

| | Flexural strength (MPa) | | Water absorbance | Solubility |
|---|---|---|---|---|
| | $1^{st}$ day | $60^{th}$ day | (μg/mm³) | (μg/mm³) |
| Ex. 1 | 133 | 135 | 15.9 | 2.50 |
| Ex. 2 | 142 | 140 | 14.1 | 1.83 |
| Ex. 3 | 135 | 134 | 15.2 | 2.95 |
| Ex. 4 | 139 | 135 | 14.7 | 2.30 |
| Comp. Ex. 1 | 140 | 142 | 15.2 | 2.10 |
| Comp. Ex. 2 | 120 | 89 | 19.3 | 4.35 |
| Comp. Ex. 3 | 125 | 78 | 23.3 | 6.75 |

As can be seen from Table 2 above, when sodium fluoride (Comparative Example 2) or fluoroaluminosilicate glass (Comparative Example 3) was added, after 60 days, flexural strength was significantly deteriorated, and water absorbance and solubility were significantly increased. This behavior is considered to be due to pores provided for fluorine diffusion. In particular, fluoroaluminosilicate glass showed considerably deteriorated physical properties. This is the reason that pyromellitic glycerol dimethacrylate added to activate fluorine is acidic and very hydrophilic.

The compositions according to the present invention prepared in the Examples did not show deterioration in flexural strength and exhibited flexural strength, water absorbance and solubility, comparable to the composition of Comparative Example 1 wherein the fluorine-release organic nanotube was not added. This behavior was considered to be due to the fact that, by using the fluorine-release organic nanotube, formation of large voids can be prevented and shape-sustainability can be excellent, although fluorine was diffused and released.

Accordingly, the composition of the present invention does not exhibit fatal disadvantages (e.g., deterioration in flexural strength, and increases in water absorbance and solubility) of conventional fluorine release-type dental compositions. That is, the dental composition exerts superior sustained-fluorine release and does not injure physical properties required for dental restorative composites, when added to the dental restorative composites.

As apparent from the fore-going, the dental composition according to the present invention comprises an organic nanotube containing an antibacterial/anticariogenic material capable of exhibiting superior compatibility and affinity with the organic matrix, and inhibiting or preventing tooth decay, thus uniformly and continuously exhibiting anticariogenic and antibacterial activities to hard tissues of teeth, while avoiding deterioration in physical properties required for the dental material.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A dental composition comprising:
   unsaturated double bond-containing monomers and/or oligomers;
   a catalytic amount of polymerization initiator to initiate polymerization; and
   a filler,
   wherein the dental composition comprises an organic nanotube containing an antibacterial or anticariogenic material to inhibit or prevent tooth decay;
   wherein the antibacterial/anticariogenic material is a fluorine compound, the organic nanotube has a hollow in which the antibacterial/anticariogenic material is contained, and both terminals of the organic nanotube are open for providing pathways allowing the antibacterial/anticariogenic material to be released from the organic nanotube, and
   wherein the organic nanotube is made from materials selected from the group consisting of methacryl, acryl, epoxy, styrene polymers, and combinations and copolymers thereof and present in an amount of 0.1 to 7% by weight, based on the total weight of the composition.

2. The dental composition according to claim 1, wherein the organic nanotube has a porous structure.

3. The dental composition according to claim 1, wherein the organic nanotube has a diameter of 10 to 3,000 nm and a length of 0.1 to 100 μm.

4. The dental composition according to claim 1, wherein the organic nanotube is prepared by a template, phase-separation, self-assembly, melt-blowing, co-axial spinning, electro spinning, or co-axial electro spinning methods.

5. The dental composition according to claim 1, wherein the fluorine compound is selected from the group consisting of aluminum fluoride, sodium fluoride, calcium fluoride, magnesium fluoride, potassium fluoride and combinations thereof.

6. The dental composition according to claim 1, wherein the unsaturated double bond-containing monomers and/or oligomers are present in an amount of 10 to 99% by weight, based on a total weight of the composition.

7. The dental composition according to claim 1, wherein the unsaturated double bond-containing monomers and/or oligomers are methyl methacrylate (MMA) monomers.

8. The dental composition according to claim 7, wherein the methyl methacrylate (MMA) monomers are selected from the group consisting of 2,2-bis-(4-(2-hydroxy-3-methacryloyloxypropoxy)phenyl)propane (Bis-GMA), ethylene glycol dimethacrylate (EGDMA), triethylene glycol dimethacrylate (TEGDMA), ethoxylate bisphenol A dimethacrylate (Bis-EMA) and urethane dimethacrylate (UDMA) monomers and combinations thereof.

9. The dental composition according to claim 1, wherein the dental composition is a dental restorative composition.

* * * * *